US008883140B2

(12) United States Patent
Siegert et al.

(10) Patent No.: US 8,883,140 B2

(45) Date of Patent: Nov. 11, 2014

(54) STABILIZED LIQUID TENSIDE PREPARATION COMPRISING ENZYMES

(71) Applicant: Henkel AG & Co. KGaA, Duesseldorf (DE)

(72) Inventors: Petra Siegert, Haan (DE); Marion Merkel, Cologne (DE); Hendrik Hellmuth, Duesseldorf (DE); Timothy O'Connell, Duesseldorf (DE); Karl-Heinz Maurer, Erkrath (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/749,879

(22) Filed: Jan. 25, 2013

(65) Prior Publication Data

US 2013/0142771 A1 Jun. 6, 2013

Related U.S. Application Data

(63) Continuation of application No. PCT/EP2011/061797, filed on Jul. 12, 2011.

(30) Foreign Application Priority Data

Jul. 27, 2010 (DE) ......................... 10 2010 038 497

(51) Int. Cl.

| | |
|---|---|
| ***A61K 38/54*** | (2006.01) |
| ***C12N 9/96*** | (2006.01) |
| ***D06M 16/00*** | (2006.01) |
| ***C12S 11/00*** | (2006.01) |
| ***C11D 3/33*** | (2006.01) |
| ***C11D 3/386*** | (2006.01) |

(52) U.S. Cl.

CPC .............. *C11D 3/38663* (2013.01); *C11D 3/33* (2013.01)

USPC .......... 424/94.3; 435/188; 435/264; 510/392; 510/393; 510/276

(58) Field of Classification Search

USPC ........................................................ 424/94.3

See application file for complete search history.

(56) References Cited

U.S. PATENT DOCUMENTS

| | | | |
|---|---|---|---|
| 2004/0259222 | A1 | 12/2004 | Breves et al. |
| 2005/0003419 | A1 | 1/2005 | Breves et al. |
| 2009/0170745 | A1 | 7/2009 | Merkel et al. |
| 2009/0275493 | A1 | 11/2009 | Siegert et al. |

FOREIGN PATENT DOCUMENTS

| | | | |
|---|---|---|---|
| EP | 0478050 | A1 | 4/1992 |
| EP | 0511456 | A1 | 11/1992 |
| GB | 1243784 | | 8/1971 |
| WO | 91/02792 | A1 | 3/1991 |
| WO | 92/19707 | A1 | 11/1992 |
| WO | 93/18140 | A1 | 9/1993 |
| WO | 95/23221 | A1 | 8/1995 |
| WO | 96/21716 | A1 | 7/1996 |
| WO | 96/34946 | A1 | 11/1996 |
| WO | 96/41859 | A1 | 12/1996 |
| WO | 01/44452 | A1 | 6/2001 |
| WO | 02/08398 | A2 | 1/2002 |
| WO | 02/29024 | A1 | 4/2002 |
| WO | 03/057246 | A1 | 7/2003 |
| WO | 2007/079938 | A2 | 7/2007 |
| WO | 2007/113241 | A1 | 10/2007 |
| WO | 2008/007319 | A2 | 1/2008 |
| WO | 2008/116915 | A1 | 10/2008 |

OTHER PUBLICATIONS

PCT International Search Report (PCT/EP2011/061797) dated Jul. 3, 2012.

Delmar et al, "A Sensitive New Substrate for Chymotrypsin", Analytical Biochemistry, vol. 99, pp. 316-320, 1979.

Van Raay et al, "The Determination of Proteolytic Activity in Enzyme Concentrates and Enzyme Containing Detergents", Tenside Detergents, vol. 7, Issue 3, pp. 125-132, 1970.

Gornall et al, "Determination of Serum Proteins by Means of the Biuret Reaction", Journal of Biological Chemistry, vol. 177, pp. 751-766, 1948.

*Primary Examiner* — Taeyoon Kim

*Assistant Examiner* — Srikanth Patury

(74) *Attorney, Agent, or Firm* — David K. Benson

(57) ABSTRACT

A hydrolytic enzyme is stabilized in a liquid surfactant preparation using a component that stabilizes the hydrolytic enzyme and encompasses an oligoaminobiphenyl oligocarboxylic acid.

11 Claims, No Drawings

STABILIZED LIQUID TENSIDE PREPARATION COMPRISING ENZYMES

FIELD OF THE INVENTION

The present invention generally relates to liquid enzyme-containing surfactant preparations such as those utilized, for example, for washing, cleaning, or disinfecting, and more particularly relates to a liquid surfactant preparation of this kind in which a hydrolytic enzyme is stabilized. The invention further relates to uses of enzyme stabilizers, and to methods in which enzymes stabilized in this fashion are used. The invention further relates to enzyme preparations stabilized in this manner.

BACKGROUND OF THE INVENTION

Problems relating to the shelf stability of enzyme-containing surfactant preparations, for example of washing, cleaning, or disinfecting agents, are known from the existing art. This problem is especially acute with liquid enzyme-containing surfactant preparations, for example liquid washing or cleaning agents. After only a short time they lose a significant degree of enzymatic, in particular hydrolytic, and especially proteolytic activity. The surfactant preparation, for example the washing, cleaning, or disinfecting agent, then no longer exhibits optimum cleaning performance. One objective in the context of the development of enzyme-containing surfactant preparations is therefore to stabilize the contained enzymes and to protect them from denaturing and/or cleavage and/or degradation, in particular during storage and/or during utilization of the surfactant preparation. Hydrolytic enzymes in particular, and especially proteases, are of interest in this regard.

Boric acid and boric acid derivatives occupy a prominent position among the enzyme stabilizers that are effective in surfactant preparations even at a comparatively low concentration. International patent application WO 96/21716 A1, for example, discloses that boric acid derivatives and boronic acid derivatives acting as protease inhibitors are suitable for stabilizing enzymes in liquid preparations, among them washing and cleaning agents. A selection of boronic acid derivatives as stabilizers is disclosed, for example, in international patent application WO 96/41859 A1. WO 92/19707 A1 and EP 478050 A1 present meta- and/or para-substituted phenylboronic acids as enzyme stabilizers. Complexes of boric acids and boric acid derivatives with aromatic compounds as enzyme stabilizers in liquid detergent compositions are disclosed in EP 511456 A.

Boric acids and boric acid derivatives have the disadvantage, however, that they form undesired secondary products with other ingredients of a surfactant preparation, in particular washing-, cleaning-, or disinfecting-agent ingredients, so that they are no longer available in the relevant agents for the desired cleaning purpose, or in fact remain behind, for example on the washed item, as a contaminant. In addition, boric acids and borates are increasingly being regarded as disadvantageous in environmental terms.

The underlying object of the present invention is to make available a liquid surfactant preparation having stabilized hydrolytic enzymes. The surfactant preparation should preferably contain fewer boron-containing compounds as enzyme stabilizers.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A liquid surfactant preparation encompassing a hydrolytic enzyme and a component stabilizing the hydrolytic enzyme, wherein the component stabilizing the hydrolytic enzyme encompasses an oligoaminobiphenyl oligocarboxylic acid.

Use of a component that encompasses an oligoaminobiphenyl oligocarboxylic acid to stabilize a hydrolytic enzyme in a liquid surfactant preparation.

A method, in particular a washing or cleaning method, in which a hydrolytic enzyme, in particular one that is selected from the group consisting of protease, amylase, cellulase, glycosidase, hemicellulase, mannanase, xylanase, xyloglucanase, xanthanase, pectinase, β-glucosidase, carrageenase, lipase, or mixtures thereof, in particular a protease, is stabilized in a washing bath by a component that stabilizes the hydrolytic enzyme and encompasses an oligoaminobiphenyl oligocarboxylic acid.

A liquid enzyme preparation encompassing a hydrolytic enzyme and a component stabilizing the hydrolytic enzyme, wherein the component stabilizing the hydrolytic enzyme encompasses an oligoaminobiphenyl oligocarboxylic acid, in particular a diaminobiphenyl dicarboxylic acid, and particularly preferably 3,3-diamino-[1,1-biphenyl]-2,4-dicarboxylic acid.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has been found that an oligoaminobiphenyl oligocarboxylic acid keeps a hydrolytic enzyme, in particular a protease, advantageously stable in a liquid surfactant preparation, for example in a liquid washing, cleaning, or disinfecting agent. This opens up the possibility of using fewer boron-containing compounds as enzyme stabilizers in liquid surfactant preparations. It is possible in particular to partly or, by preference, entirely eliminate boric acid as an enzyme stabilizer in a liquid surfactant preparation, so that the liquid surfactant preparation can be free of boric acid. In particularly advantageous embodiments, a surfactant preparation of this kind can ideally be free of boron.

In addition, these compounds have the advantage that they already exert their stabilizing effect at low to very low concentrations. They moreover possess good water solubility. They can therefore easily be incorporated and easily utilized in liquid surfactant preparations, in particular in liquid washing, cleaning, or disinfecting agents or in a washing bath constituted by such a surfactant preparation. Precipitation during storage is moreover decreased or entirely avoided.

The component stabilizing the hydrolytic enzyme encompasses an oligoaminobiphenyl oligocarboxylic acid. An oligoaminobiphenyl oligocarboxylic acid in the context of the present invention is described by formula (I) below:

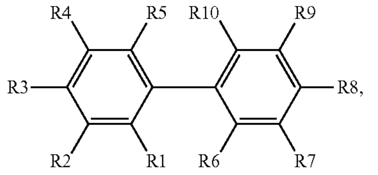

(I)

where R1, R2, R3, R4, R5, R6, R7, R8, R9, and R10 are each —$NH_2$, —COOH, or —H, where at least two of the residues R1 to R10 are $NH_2$, and at least two of the residues R1 to R10 are —COOH and the further residues are —H. By preference, those residues R1 to R10 that are —$NH_2$ and those residues R1 to R10 that are —COOH are located on adjacent carbon atoms, i.e. in the ortho position with respect to one another.

More preferably, exactly two of the residues R1 to R10 are —$NH_2$ and two of the residues R1 to R10 are —COOH, and the further residues are —H. This kind of embodiment of the invention is consequently characterized in that the oligoaminobiphenyl oligocarboxylic acid is a diaminobiphenyl dicarboxylic acid. Particularly preferably, R1 is —COOH, R2 is —$NH_2$, R7 is —$NH_2$, R8 is —COOH, and R3, R4, R5, R6, R9, R10 are each —H. In one such particularly preferred embodiment of the invention, the oligoaminobiphenyl oligocarboxylic acid is 3,3-diamino-[1,1-biphenyl]-2,4-dicarboxylic acid, which is indicated in formula (II) below:

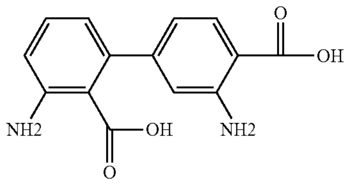 [SMILES: Nc1cc(-c2cccc(N)c2C(=O)O)ccc1C(=O)O]

Also considered an oligoaminobiphenyl oligocarboxylic acid in the context of the invention are derivatives of said compounds. Such derivatives comprise further chemical modifications; in particular they can be glycosylated, oxidized, N-methylated, N-formylated, N-acetylated on one or more of the amino groups, or can contain one or more methyl, amino, nitro, chloro, fluoro, bromo, hydroxyl, carboxyl, formyl, ethyl, acetyl, t-butyl, anisyl, benzyl, trifluoroacetyl, N-hydroxysuccinimide, t-butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulfenyl, 4-toluenesulfonyl, pentafluorophenyl, diphenylmethyl, 2-chlorobenzyloxycarbonyl, 2,4,5-trichlorophenyl, 2-bromobenzyloxycarbonyl, 9-fluorenylmethyoxycarbonyl, triphenylmethyl, 2,2,5,7,8-pentamethylchroman-6-sulfonyl residues or groups, or combinations thereof.

All compounds that are provided in the context of the present invention as a component stabilizing the hydrolytic enzyme can be present in the surfactant preparation in all protonated or deprotonated forms. In addition, all such compounds, in particular deprotonated forms thereof, can be associated with cations. Preferred cations in this regard are divalent cations, in particular calcium ions ($Ca^{2+}$), magnesium ions ($Mg^{2+}$), and zinc ions ($Zn^{2+}$). Calcium ions ($Ca^{2+}$) are particularly preferred. The compounds can moreover be present in all possible stereoisomeric forms.

The component stabilizing the hydrolytic enzyme can be made up entirely of the aforesaid compound, so that the component stabilizing the hydrolytic enzyme is the oligoaminobiphenyl oligocarboxylic acid. Alternatively, the component stabilizing the hydrolytic enzyme can encompass further compounds, so that the oligoaminobiphenyl oligocarboxylic acid is part of the component stabilizing the hydrolytic enzyme.

The oligoaminobiphenyl oligocarboxylic acid is contained in the liquid surfactant preparation by preference in a quantity from 0.000001 to 10 wt %, and increasing preferably from 0.00001 to 5 wt %, from 0.001 to 3 wt %, from 0.01 to 2.5 wt %, from 0.1 to 2.25 wt %, and from 0.5 to 2 wt %.

A hydrolytic enzyme is a hydrolase (EC 3.X.X.X) and thus an enzyme that hydrolytically cleaves esters, ethers, peptides, glycosides, acid anhydrides, or carbon-carbon bonds in a reversible reaction. The hydrolytic enzyme therefore catalyzes the hydrolytic cleavage of substances as defined by: $A–B+H_2O<–>AH+B–OH$. Hydrolases form the third main class in the EC classification of enzymes. The EC (Enzyme Commission) numbers constitute a numerical classification system for enzymes. Each EC number is made up of four numbers separated by periods; the first digit identifies one of the six main enzyme classes, and hydrolases (EC 3.X.X.X) correspondingly represent the third main class. Its representatives are proteases, peptidases, nucleases, phosphatases, glycosidases, and esterases.

The hydrolytic enzyme is contained in the liquid surfactant preparation by preference in a quantity from $1\times10^{-8}$ to 5 weight percent, based on active protein. The hydrolytic enzyme is contained in the liquid surfactant preparation preferably from 0.001 to 5 wt %, more preferably from 0.01 to 5 wt %, even more preferably from 0.05 to 4 wt %, and particularly preferably from 0.075 to 3.5 wt %. The hydrolytic enzyme can furthermore be bound covalently or noncovalently to a carrier substance, and/or embedded into encasing substances, for example in order to protect it additionally from premature inactivation. The protein concentration in the surfactant preparation can be determined with the aid of known methods, for example the BCA method (bicinchoninic acid; 2,2'-biquinolyl-4,4'-dicarboxylic acid) or the biuret method (A. G. Gornall, C. S. Bardawill and M. M. David, J. Biol. Chem., 177 (1948), pp. 751-766).

In a further preferred embodiment, a surfactant preparation according to the present invention is characterized in that the hydrolytic enzyme is a protease, amylase, cellulase, glycosidase, hemicellulase, mannanase, xylanase, xyloglucanase, xanthanase, pectinase, β-glucosidase, carrageenase, or a lipase, or is a mixture that encompasses at least two of said enzymes. Particularly preferably, the hydrolytic enzyme is a protease, more preferably a serine protease, more preferably a subtilase, and very particularly preferably a subtilisin. It has been found that proteases, in particular such proteases, are stabilized particularly well by the component stabilizing the hydrolytic enzyme in a surfactant preparation according to the present invention. The reason is that the shelf stability of the enzymes, and in particular also that of proteases, is a general problem especially for washing, cleaning, or disinfecting agents.

Examples of proteases are the subtilisins BPN' from *Bacillus* amyloliquefaceans and Carlsberg from *Bacillus licheniformis*, protease PB92, subtilisins 147 and 309, the protease from *Bacillus lentus*, subtilisin DY, and the enzymes (to be classified, however, as subtilases and no longer as subtilisins in the strict sense) thermitase, proteinase K, and the proteases TW3 and TW7. Subtilisin Carlsberg is obtainable in further developed form under the trade name Alcalase® from Novozymes A/S, Bagsvaerd, Denmark. Subtilisins 147 and 309 are marketed by Novozymes under the trade names Esperase® and Savinase®, respectively. The protease variants listed under the designation BLAP® are derived from the protease from *Bacillus lentus* DSM 5483. Other usable proteases are, for example, the enzymes obtainable under the trade names Durazym®, Relase®, Everlase®, Nafizym®, Natalase®, Kannase®, and Ovozyme® from Novozymes, under the trade names Purafect®, Purafect® OxP, Purafect® Prime, Excellase®, and Properase® from Danisco/Genencor, under the trade name Protosol® from Advanced Biochemicals Ltd., Thane, India, under the trade name Wuxi® from Wuxi Snyder Bioproducts Ltd., China, under the trade names Proleather® and Protease P® from Amano Pharmaceuticals Ltd., Nagoya, Japan, and under the designation Proteinase K-16 from Kao Corp., Tokyo, Japan. The proteases from *Bacillus gibsonii* and *Bacillus pumilus*, which are disclosed in international patent applications WO 08/086,916 and WO 07/131,656, are also used with particular preference. Further advantageously usable proteases are disclosed in patent applications WO 91/02792, WO 08/007,319, WO 93/18140, WO 01/44452, GB 1243784, WO 96/34946, WO 02/029024, and WO 03/057246. Further usable proteases are those that are naturally present in the microorganisms *Stenotrophomonas maltophilia*, in particular *Stenotrophomonas maltophilia* K279a, *Bacillus intermedius*, and *Bacillus sphaericus*.

Examples of amylases are the α-amylases from *Bacillus licheniformis*, from *Bacillus amyloliquefaciens*, or from *Bacillus stearothermophilus*, and in particular the further developments thereof improved for use in washing or cleaning agents. The enzyme from *Bacillus licheniformus* is available from the Novozymes company under the name Termamyl®, and from Danisco/Genencor under the name Purastar® ST. Further developed products of this α-amylase are available from Novozymes under the trade names Duramyl® and Termamyl® ultra, from Danisco/Genencor under the name Purastar® OxAm, and from Daiwa Seiko Inc., Tokyo, Japan, as Keistase®. The α-amylase from *Bacillus amyloliquefaciens* is marketed by Novozymes under the name BAN®, and derived variants of the α-amylase from *Bacillus stearothermophilus* are marketed, again by Novozymes, under the names BSG® and Novamyl®. Additionally to be highlighted for this purpose are the α-amylase from *Bacillus* sp. A 7-7 (DSM 12368) and the cyclodextrin-glucanotransferase (CGTase) from *Bacillus agaradherens* (DSM 9948). Also usable are the amylolytic enzymes that are disclosed in international patent applications WO 03/002711, WO 03/054177, and WO 07/079,938. Fusion products of all the aforesaid molecules are likewise usable. The further developments of the α-amylase from *Aspergillus niger* and *A. oryzae*, obtainable from Novozymes under the trade names Fungamyl®, are also suitable. Further advantageously usable commercial products are, for example, Amylase-LT® and Stainzyme® or Stainzyme Ultra® or Stainzyme Plus®, the latter likewise from Novozymes. Variants of these enzymes obtainable by point mutations can also be used according to the present invention.

Examples of cellulases (endoglucanases, EG) are the fungus-based cellulase preparation rich in endoglucanase (EG), or its further developments, offered by the Novozymes company under the trade name Celluzyme®. The products Endolase® and Carezyme®, likewise obtainable from the Novozymes company, are based on the 50 kD EG and 43 kD EG, respectively, from *Humicola insolens* DSM 1800. Further usable commercial products of this company are Cellusoft®, Renozyme®, and Celluclean®. Also usable are, for example, cellulases that are available from the AB Enzymes company, Finland, under the trade names Ecostone® and Biotouch® and that are based at least in part on the 20 kD EG from Melanocarpus. Other cellulases of the AB Enzymes company are Econase® and Ecopulp®. Other suitable cellulases are from *Bacillus* sp. CBS 670.93 and CBS 669.83, the one from *Bacillus* sp. CBS 670.93 being obtainable from the Danisco/Genencor company under the trade name Puradax®. Other usable commercial products of the Danisco/Genencor company are "Genencor detergent cellulase L" and IndiAge® Neutra.

Further preferred hydrolytic enzymes are those grouped under the term "glycosidases" (EC 3.2.1.X). These include in particular arabinases, fucosidases, galactosidases, galactanases, arabico-galactan-galactosidases, mannanases (also called mannosidases or mannases), glucuronosidases, agarase, carrageenases, pullulanases, β-glucosidases, xyloglucanases (xylanases), xanthanases, and pectin-degrading enzymes (pectinases). Preferred glycosidases are also grouped under the term "hemicellulases." Included among the hemicellulases are, in particular, mannanases, xyloglucanases (xylanases), β-glucosidases, and carrageenases, as well as furthermore pectinases, pullulanases, and β-glucanases. Pectinases are pectin-degrading enzymes, the hydrolytic pectin-degrading enzymes belonging in particular to the enzyme classes EC 3.1.1.11, EC 3.2.1.15, EC 3.2.1.67, and EC 3.2.1.82. Also considered pectinases in the context of the present invention are enzymes having the designations pectate lyase, pectin esterase, pectin demethoxylase, pectin methoxylase, pectin methylesterase, pectase, pectin methylesterase, pectinoesterase, pectin pectylhydrolase, pectin depolymerase, endopolygalacturonase, pectolase, pectin hydrolase, pectin polygalacturonase, endopolygalacturonase, poly-α-1,4-galacturonide glycanohydrolase, endogalacturonase, endo-D-galacturonase, galacturan 1,4-α-galacturonidase, exopolygalacturonase, poly(galacturonate) hydrolase, exo-D-galacturonase, exo-D-galacturonanase, exopoly-D-galacturonase, exopoly-α-galacturonosidase, exopolygalacturonosidase, or exopolygalacturanosidase.

Examples of enzymes suitable in this context are obtainable, for example, under the names Gamanase®, Pektinex AR®, or Pectaway® from the Novozymes company, under the name Rohapec® B1L from the AB Enzymes company, and under the name Pyrolase® from Diversa Corp., San Diego, Calif., USA. The ®-glucanase recovered from *Bacillus subtilis* is available under the name Cereflo® from the Novozymes company. Glycosidases or hemicellulases particularly preferred according to the present invention are mannanases, which are marketed e.g. under the trade names Mannaway® by Novozymes or Purabrite® by Danisco/Genencor.

Examples of lipases or cutinases are the lipases obtainable originally from *Humicola lanuginosa* (*Thermomyces lanuginosus*) or lipases further developed therefrom, in particular those having the D96L amino acid exchange. They are marketed, for example, by the Novozymes company under the trade names Lipolase®, Lipolase® Ultra, LipoPrime®, Lipozyme®, and Lipex®. A further advantageously usable lipase is obtainable from the Novozymes company under the trade name Lipoclean®. The cutinases that were originally isolated from *Fusarium solani* pisi and *Humicola insolens* are moreover usable, for example. Similarly usable lipases are obtainable from the Amano company under the designations Lipase CE®, Lipase P®, Lipase B® or Lipase CES®, Lipase AKG®, *Bacillis* sp. Lipase®, Lipase AP®, Lipase M-AP®, and Lipase AML®. The lipases or cutinases from, for example, the Danisco/Genencor company, whose starting enzymes were originally isolated from *Pseudomonas mendocina* and *Fusarium solanii*, are usable. To be mentioned as further important commercial products are the preparations M1 Lipase® and Lipomax® originally marketed by the Gist- Brocades company (now Danisco/Genencor), and the enzymes marketed by Meito Sangyo KK, Japan, under the names Lipase MY-30®, Lipase OF®, and Lipase PL®, as well as the Lumafast® product of the Danisco/Genencor company.

The enzymes to be used in the context of the present invention can originally derive, for example, from microorganisms, e.g. of the genera *Bacillus, Streptomyces, Humicola*, or *Pseudomonas*, and/or can be produced by suitable microorganisms according to biotechnological methods known per se, e.g. by means of transgenic expression hosts, for example the genera *Escherichia, Bacillus*, or by filamentous fungi. It is emphasized that this can also involve, in particular, technical enzyme preparations of the respective enzyme, i.e. accompanying constituents can be present. The enzymes can therefore be packaged and used together with accompanying constituents, for example from fermentation, or with further stabilizers.

Enzyme "stabilization" for purposes of the invention exists when the presence of the component stabilizing the hydrolytic enzyme causes a surfactant preparation encompassing hydrolytic enzyme and a component stabilizing the hydrolytic enzyme (surfactant preparation according to the present invention) to exhibit after storage a higher enzymatic activity of the hydrolytic enzyme as compared with a control preparation that differs from the surfactant preparation according to the present invention only in that the component stabilizing the hydrolytic enzyme is absent (control). In this regard, the oligoaminobiphenyl oligocarboxylic acid is contained in the surfactant preparation according to the present invention in a quantity from 0.5 to 2 wt %. After storage, the surfactant preparation according to the present invention therefore exhibits higher residual activity of the hydrolytic enzyme as compared with the control, the preparation according to the present invention and the control exhibiting the same initial enzyme activity when storage began, and both preparations being processed in the same manner, in particular with regard to storage conditions and the determination of enzyme activity. Storage occurs, with increasing preference, for at least 24 hours, 48 hours, 72 hours, 5 days, 1 week, 13 days, 3 weeks, or 4 weeks. With further preference, storage occurs at a temperature of 20° C., 25° C., or 30° C.

The enzyme activity can occur in this regard, coordinated with the respective type of enzyme, in a manner usual in the art. Methods for determining activity are familiar to one skilled in the art of enzyme technology, and are routinely utilized by him or her. Methods for determining protease activity are disclosed, for example, in Tenside, Vol. 7 (1970), pp. 125-132. Proteolytic activity can furthermore be determined by way of the release of the para-nitroaniline (pNA) chromophore from the suc-L-Ala-L-Ala-L-Pro-L-Phe-p-nitroanilide substrate (suc-AAPF-pNA) (SEQO ID NO. 1). The protease cleaves the substrate and releases pNA. The release of pNA causes an increase in extinction at 410 nm, the time course of which is an indication of enzymatic activity (see Del Mar et al., 1979). Measurement is performed at a temperature of 25° C., at pH 8.6 and a wavelength of 410 nm. The measurement time is 5 min, with a measurement interval from 20 s to 60 s. The protease activity is preferably indicated in CPU (protease units).

The existence of enzyme stabilization is particularly preferably ascertained using a protease-containing liquid surfactant preparation which is stored for 13 days at a temperature of 30° C., and whose residual proteolytic activity is determined via the release of the para-nitroaniline (pNA) chromophore from the suc-AAPF-Pna (SEQ ID NO. 1) substrate. Very particularly preferably, the existence of enzyme stabilization in this regard is ascertained as described in the Example.

A "surfactant preparation" is to be understood in the context of the present invention as any type of composition that contains at least one surfactant. A composition of this kind preferably contains a surfactant as described below.

All liquid or flowable administration forms can serve in this context as liquid surfactant preparations. Preparations that are pourable and can have viscosities of up to several tens of thousands of mPas are "flowable" for purposes of the present invention. The viscosity can be measured with usual standard methods (e.g. Brookfield LVT-II viscosimeter at 20 rpm and 20° C., spindle 3), and is preferably in the range from 5 to 10,000 mPas. Preferred agents have viscosities from 10 to 8000 mPas, values between 120 and 3000 mPas being particularly preferred. A liquid surfactant preparation in the context of the present invention can therefore also be gel-like or paste-like; it can be present as a homogeneous solution or suspension, and can, for example, be sprayable or can be packaged in other usual administration forms.

A liquid surfactant preparation according to the present invention can be used as such or after dilution with water, in particular for cleaning textiles and/or hard surfaces. Such dilution is easily brought about by diluting a measured quantity of the surfactant preparation in a further quantity of water at specific weight ratios of surfactant preparation to water, and optionally shaking that dilution in order to ensure uniform distribution of the surfactant preparation in water. Possible weight or volume ratios of the dilutions are from 1:0 surfactant preparation:water to 1:10,000 or 1:20,000 surfactant preparation:water, by preference from 1:10 to 1:2000 surfactant preparation:water.

A "surfactant preparation" for purposes of the present invention can therefore also be the washing or cleaning bath itself. A "washing or cleaning bath" is understood as that utilization solution, containing the washing or cleaning agent, which acts on textiles or fabric (washing bath) or hard surfaces (cleaning bath) and thereby comes into contact with stains present on textiles or fabrics or hard surfaces. The washing or cleaning bath is usually produced when the washing or cleaning operation begins and the washing or cleaning agent is diluted with water, for example in a washing machine or in another suitable container.

In a preferred embodiment, the surfactant preparation is a washing, cleaning, or disinfecting agent. Included among the washing agents are all conceivable types of washing agent, in particular washing agents for textiles, carpets, or natural fibers. They can be provided for manual and/or also for automatic use. Also included among the washing agents are washing adjuvants that are dispensed into the actual washing agent in the context of manual or automatic textile laundering in order to achieve a further effect. Included among the cleaning agents are all agents, again occurring in all the aforesaid administration forms, for cleaning and/or disinfection of hard surfaces, manual and automatic dishwashing agents, carpet cleaners, scrubbing agents, glass cleaners, toilet deodorizing cleaners, etc. Lastly, textile pre- and post-treatment agents are on the one hand those agents with which the laundry item is brought into contact before actual laundering, for example in order to loosen stubborn stains, and on the other hand those that, in a step following the actual textile laundering, impart to the washed item further desirable properties such as a pleasant feel, freedom from wrinkles, or a low static charge. The fabric softeners, among others, are categorized among the last-named agents. Disinfecting agents are, for example, hand disinfecting agents, surface disinfecting agents, and equipment disinfecting agents, which can likewise occur in the administration forms mentioned. A disinfecting agent preferably brings about a germ reduction by a factor of at least $10^4$, i.e. of 10,000 germs originally capable of propagation (so-called colony-forming units or CFUs), no more than a single one survives (viruses are not regarded in this context as germs, since they have no cytoplasm and exhibit no independent metabolism). Preferred disinfecting agents bring about a germ reduction by a factor of at least $10^5$.

Anionic, nonionic, zwitterionic, and/or amphoteric surfactants can be used as surfactant(s). Mixtures of anionic and nonionic surfactants are preferred in terms of applications engineering. The total surfactant content of the liquid surfactant preparation is preferably below 60 wt %, and particularly preferably below 45 wt %, based on the total liquid surfactant preparation.

Suitable nonionic surfactants encompass alkoxylated fatty alcohols, alkoxylated fatty acid alkyl esters, fatty acid amides, alkoxylated fatty acid amides, polyhydroxy fatty acid amides, alkylphenyl polyglycol ethers, amine oxides, alkylpolyglucosides, and mixtures thereof.

The nonionic surfactants used are by preference alkoxylated, advantageously ethoxylated, in particular primary alcohols having by preference 8 to 18 carbon atoms and an average of 1 to 12 mol ethylene oxide (EO) per mol of alcohol, in which the alcohol residue can be linear or preferably methyl-branched in the 2-position, or can contain mixed linear and methyl-branched residues, such as those that are usually present in oxo alcohol residues. Particularly preferred, however, are alcohol ethoxylates having linear residues made up of alcohols of natural origin having 12 to 18 carbon atoms, e.g. from coconut, palm, tallow, or oleyl alcohol, and an average of 2 to 8 EO per mol of alcohol. The preferred ethoxylated alcohols include, for example, $C_{12-14}$ alcohols with 3 EO, 4 EO or 7 EO, $C_{9-11}$ alcohol with 7 EO, $C_{13-15}$ alcohols with 3 EO, 5 EO, 7 EO, or 8 EO, $C_{12-18}$ alcohols with 3 EO, 5 EO or 7 EO, and mixtures thereof, such as mixtures of $C_{12-14}$ alcohol with 3 EO and $C_{12-18}$ alcohol with 7 EO. The degrees of ethoxylation indicated represent statistical averages, which can correspond to an integer or a fractional number for a specific product. Preferred alcohol ethoxylates exhibit a restricted distribution of homologs (narrow range ethoxylates, NRE). In addition to these nonionic surfactants, fatty alcohols with more than 12 EO can also be used. Examples of these are tallow fatty alcohol with 14 EO, 25 EO, 30 EO, or 40 EO. Nonionic surfactants that contain EO and PO groups together in the molecule are also usable according to the present invention. A mixture of a (more highly) branched ethoxylated fatty alcohol and an unbranched ethoxylated fatty alcohol is also suitable, for example a mixture of a $C_{16-18}$ fatty alcohol with 7 EO and 2-propylheptanol with 7 EO. Particularly preferably, the surfactant preparation contains a $C_{12-18}$ fatty alcohol with 7 EO or a $C_{13-15}$ oxoalcohol with 7 EO as a nonionic surfactant.

The nonionic surfactant content is preferably 3 to 40 wt %, by preference 5 to 30 wt %, and in particular 7 to 20 wt %, based in each case on the total surfactant preparation.

In addition to the nonionic surfactants, the surfactant preparation can also contain anionic surfactants. Sulfonates, sulfates, soaps, alkylphosphates, anionic silicone surfactants, and mixtures thereof are used by preference as an anionic surfactant.

Possibilities as surfactants of the sulfonate type are, by preference, $C_{9-13}$ alkylbenzenesulfonates, olefinsulfonates, i.e. mixtures of alkene- and hydroxyalkanesulfonates, and disulfonates, for example such as those obtained from $C_{12-18}$ monoolefins having a terminal or internal double bond, by sulfonation with gaseous sulfur trioxide and subsequent alkaline or acid hydrolysis of the sulfonation products. Also suitable are $C_{12-18}$ alkanesulfonates and the esters of α-sulfo fatty acids (estersulfonates), for example the α-sulfonated methyl esters of hydrogenated coconut, palm kernel, or tallow fatty acids.

Preferred alk(en)yl sulfates are the alkali, and in particular sodium, salts of the sulfuric acid semi-esters of the $C_{12}$ to $C_{18}$ fatty alcohols, for example from coconut fatty alcohol, tallow fatty alcohol, lauryl, myristyl, cetyl, or stearyl alcohol, or the $C_{10}$ to $C_{20}$ oxo alcohols, and those semi-esters of secondary alcohols of those chain lengths. For purposes of washing technology, the $C_{12}$ to $C_{16}$ alkyl sulfates and $C_{12}$ to $C_{15}$ alkyl sulfates, as well as $C_{14}$ to $C_{15}$ alkyl sulfates, are preferred. 2,3-Alkyl sulfates are also suitable anionic surfactants.

The sulfuric acid monoesters of straight-chain or branched $C_{7-21}$ alcohols ethoxylated with 1 to 6 mol ethylene oxide, such as 2-methyl-branched $C_{9-11}$ alcohols with an average of 3.5 mol ethylene oxide (EO), or $C_{12-18}$ fatty alcohols with 1 to 4 EO, are also suitable.

Soaps are also suitable anionic surfactants. Saturated and unsaturated fatty acid soaps, such as the salts of lauric acid, myristic acid, palmitic acid, stearic acid, (hydrogenated) erucic acid, and behenic acid, are suitable, as are soap mixtures derived in particular from natural fatty acids, e.g. coconut, palm-kernel, olive-oil, or tallow fatty acids.

The anionic surfactants, including the soaps, can be present in the form of their sodium, potassium, magnesium, or ammonium salts. The anionic surfactants are preferably present in the form of their ammonium salts. Further preferred counterions for the anionic surfactants are also the protonated forms of choline, triethylamine, or methylethylamine.

The concentration of anionic surfactants in a surfactant preparation can be 1 to 40 wt %, by preference 5 to 30 wt %, and very particularly preferably 10 to 25 wt %, based in each case on the total surfactant preparation.

In a further embodiment, the surfactant preparation is characterized in that it additionally encompasses at least one further ingredient that is selected from the group consisting of builder, nonaqueous solvent, acid, water-soluble salt, thickening agent, disinfecting ingredient, and combinations thereof.

The addition of one or more of the further ingredient(s) proves advantageous because additionally improved cleaning performance and/or disinfection is thereby achieved. The improved cleaning performance and/or disinfection is preferably based on a synergistic interaction of at least two ingredients. A synergy of this kind can be achieved in particular by way of the combination of the hydrolytic enzyme, by preference a protease, with one of the builders described below and/or with one of the nonaqueous solvents described below and/or with one of the acids described below and/or with one of the water-soluble salts described below and/or with one of the thickening agents described below and/or with one of the disinfecting ingredients described below.

Silicates, aluminum silicates (in particular zeolites), carbonates, salts of organic di- and polycarboxylic acids, and mixtures of said substances may be recited, in particular, as builders that can be contained in the surfactant preparation.

Organic builders that can be present in the surfactant preparation are, for example, the polycarboxylic acids usable in the form of the sodium salts thereof, "polycarboxylic acids" being understood as those carboxylic acids that carry more than one acid function. These are, for example, citric acid, adipic acid, succinic acid, glutaric acid, malic acid, tartaric acid, maleic acid, fumaric acid, sugar acids, aminocarboxylic acids, nitrilotriacetic acid (NTA), methylglycinediacetic acid (MGDA), and derivatives thereof, as well as mixtures thereof. Preferred salts are the salts of the polycarboxylic acids such as citric acid, adipic acid, succinic acid, glutaric acid, tartaric acid, sugar acids, and mixtures thereof.

Polymeric polycarboxylates are additionally suitable as builders. These are, for example, the alkali-metal salts of polyacrylic acid or of polymethacrylic acid, for example those having a relative molecular weight from 600 to 750,000 g/mol.

Suitable polymers are, in particular, polyacrylates that preferably have a molecular weight from 1000 to 15,000 g/mol. Of this group in turn, the short-chain polyacrylates, which have molar masses from 1000 to 10,000 g/mol and particularly preferably from 1000 to 5000 g/mol, may be preferred because of their superior solubility.

Also suitable are copolymeric polycarboxylates, in particular those of acrylic acid with methacrylic acid and of acrylic acid or methacrylic acid with maleic acid. To improve water solubility, the polymers can also contain allylsulfonic acids, such as allyloxybenzenesulfonic acid and methallylsulfonic acid, as monomers.

It is preferred, however, to use soluble builders, for example citric acid, or acrylic polymers having a molar mass from 1000 to 5000 g/mol, in the liquid surfactant preparation.

The molar masses indicated for polymeric polycarboxylates are, for purposes of this document, weight-average molar masses Mw of the respective acid form that were determined in principle by means of gel permeation chromatography (GPC), a UV detector having been used. The measurement was performed against an external polyacrylic acid standard that yields realistic molecular weight values because of its structural affinity with the polymers being investigated. These indications deviate considerably from the molecular weight indications in which polystyrenesulfonic acids are used as a standard. The molar masses measured against polystyrenesulfonic acids are as a rule much higher than the molar masses indicated in this document.

Organic builder substances of this kind can be contained, if desired, in quantities of up to 40 wt %, in particular up to 25 wt %, and by preference from 1 wt % to 8 wt %. Quantities close to the aforesaid upper limit are used by preference in pasty or liquid, in particular water-containing, surfactant preparations.

The surfactant preparations according to the present invention are liquid and by preference contain water as a principal solvent. Additionally or alternatively thereto, nonaqueous solvents can be added to the surfactant preparation. Suitable nonaqueous solvents encompass monovalent or polyvalent alcohols, alkanolamines, or glycol ethers, provided they are miscible with water in the concentration range indicated. The solvents are by preference selected from ethanol, n-propanol, isopropanol, butanols, glycol, propanediol, butanediol, glycerol, diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol monomethyl ether, dipropylene glycol monoethyl ether, diisopropylene glycol monomethyl ether, diisopropylene glycol monoethyl ether, methoxytriglycol, ethoxytriglycol, butoxytriglycol, 1-butoxyethoxy-2-propanol, 3-methyl-3-methoxybutanol, propylene glycol t-butyl ether, di-n-octyl ether, and mixtures of these solvents. It is preferred, however, that the surfactant preparation contain a polyol as a nonaqueous solvent. The polyol can encompass, in particular, glycerol, 1,2-propanediol, 1,3-propanediol, ethylene glycol, diethylene glycol, and/or dipropylene glycol. Particularly preferably, the surfactant preparation contains a mixture of a polyol and a monovalent alcohol. Nonaqueous solvents can be used in the surfactant preparation in quantities between 0.5 and 15 wt %, but preferably below 12 wt %.

In order to establish a desired pH that does not result of itself from mixture of the other components, the surfactant preparations can contain system-compatible and environmentally compatible acids, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium hydroxides or alkali hydroxides. pH regulators of this kind are contained in the surfactant preparations in quantities by preference not above 20 wt %, in particular from 1.2 wt % to 17 wt %.

A surfactant preparation for purposes of the invention can furthermore contain one or more water-soluble salts, which serve e.g. to adjust viscosity. These can be inorganic and/or organic salts. Usable inorganic salts are selected in this context by preference from the group encompassing colorless water-soluble halides, sulfates, sulfites, carbonates, hydrogencarbonates, nitrates, nitrites, phosphates, and/or oxides of the alkali metals, of the alkaline earth metals, of aluminum, and/or of the transition metals; ammonium salts are also usable. Halides and sulfates of the alkali metals are particularly preferred in this context; the inorganic salt is therefore preferably selected from the group encompassing sodium chloride, potassium chloride, sodium sulfate, potassium sulfate, and mixtures thereof. Usable organic salts are, for example, colorless water-soluble alkali-metal, alkaline-earth-metal, ammonium, aluminum, and/or transition-metal salts of carboxylic acids. The salts are by preference selected from the group encompassing formate, acetate, propionate, citrate, malate, tartrate, succinate, malonate, oxalate, lactate, and mixtures thereof.

For thickening, a surfactant preparation according to the present invention can contain one or more thickening agents. The thickening agent is preferably selected from the group encompassing xanthan, guar, carrageenan, agar-agar, gellan, pectin, locust bean flour, and mixtures thereof. These compounds are effective thickening agents even in the presence of inorganic salts. In a particularly preferred embodiment, the surfactant preparation contains xanthan as a thickening agent, since xanthan thickens effectively even in the presence of high salt concentrations and prevents macroscopic separation of the continuous phase. In addition, the thickening agent stabilizes the continuous, surfactant-poor phase and prevents macroscopic phase separation.

Alternatively or in supplementary fashion, (meth)acrylic acid (co)polymers can also be used as thickening agents. Suitable acrylic and methacrylic (co)polymers encompass, for example, the high-molecular-weight homopolymers of acrylic acid crosslinked with a polyalkenyl polyether, in particular an allyl ether, of sucrose, pentaerythritol, or propylene (INCI name, according to "International Dictionary of Cosmetic Ingredients" of the Cosmetic, Toiletry and Fragrance Association (CFTA): Carbomer), which are also referred to as carboxyvinyl polymers. Polyacrylic acids of this kind are obtainable, inter alia, under the trade names Polygel® and Carbopol®. Also suitable, for example, are the following acrylic acid copolymers: (i) copolymers of two or more monomers from the group of acrylic acid, methacrylic acid, and their simple esters, formed by preference with $C_{1-4}$ alkanols (INCI: Acrylates Copolymer), which are obtainable, for example, under the trade names Aculyn®, Acusol®, or Tego® Polymer, (ii) crosslinked high-molecular-weight acrylic acid copolymers, included among which are, for example, the copolymers, crosslinked with an allyl ether of sucrose or of pentaerythritol, of $C_{10-30}$ alkyl acrylates with one or more monomers from the group of acrylic acid, methacrylic acid, and their simple esters formed preferably with $C_{1-4}$ alkanols (INCI: Acrylates/$C_{10-30}$ Alkyl Acrylate Crosspolymer), and which are obtainable, for example, under the trade name Carbopol®. Further suitable polymers are (meth) acrylic acid (co)polymers of the Sokalan® type.

It may be preferred for the surfactant preparation according to the present invention to contain a (meth)acrylic acid (co) polymer in combination with a further thickening agent, by preference xanthan. The surfactant preparation can contain 0.05 to 1.5 wt %, and by preference 0.1 to 1 wt % thickening agent, based in each case on the total surfactant preparation. The quantity of thickening agent used depends here on the nature of the thickening agent and the desired degree of thickening.

A "disinfecting ingredient" is understood in particular as ingredients that possess an antimicrobial or antiviral effect, i.e. that kill germs. The germ-killing effect depends in this context on the concentration of the disinfecting ingredient in the surfactant preparation; the germ-killing effect decreases as the concentration of the disinfecting ingredient decreases, or as the dilution of the surfactant preparation increases.

A preferred disinfecting ingredient is ethanol or propanol. These monovalent alcohols are often used in disinfecting agents, and also in cleaning agents in general, because of their solvent properties and their germ-killing effect. The term "propanol" here encompasses both 1-propanol (n-propanol) and 2-propanol (isopropanol). Ethanol and/or propanol is contained in the surfactant preparation, for example, in a total quantity from 10 to 65 wt %, by preference 25 to 55 wt %. A further preferred disinfecting ingredient is tea tree oil. This is the essential oil of the Australian tea tree (Melaleuca alternifolia), an evergreen shrub of the Melaleuca genus native to New South Wales and Queensland, and of further tea tree species of various genera (e.g. Baeckea, Kunzea, and Leptospennum) in the Myrtaceae family. Tea tree oil is obtained by steam distillation from the leaves and twigs of these trees, and is a mixture of approx. 100 substances; among the principal constituents are (+)-terpinen-4-ol, α-terpinene, terpinolene, terpineol, pinene, myrcene, phellandrene, p-cymene, limonene, and 1,8-cineole. Tea tree oil is contained in the virucidal treatment solution, for example, in a quantity from 0.05 to 10 wt %, by preference 0.1 to 5.0 wt %. A further preferred disinfecting ingredient is lactic acid. Lactic acid, or 2-hydroxypropionic acid, is a fermentation product that is generated by a variety of microorganisms. It has mild antibiotic activity. Lactic acid is contained in the surfactant preparation, for example, in quantities of up to 10 wt %, by preference 0.2 to 5.0 wt %.

Further disinfecting ingredients are, for example, active substances from the groups of the alcohols, aldehydes, antimicrobial acids or salts thereof, carboxylic acid esters, acid amides, phenols, phenol derivatives, diphenyls, diphenylalkanes, urea derivatives, oxygen and nitrogen acetals and formals, benzamidines, isothiazoles and derivatives thereof such as isothiazolines and isothiazolinones, phthalimide derivatives, pyridine derivatives, antimicrobial surface-active compounds, guanidines, antimicrobial amphoteric compounds, quinolines, 1,2-dibromo-2,4-dicyanobutane, iodo-2-propynylbutyl carbamate, iodine, iodophores, and peroxides. Active substances preferred thereamong are selected by preference from the group encompassing 1,3-butanediol, phenoxyethanol, 1,2-propylene glycol, glycerol, undecylenic acid, citric acid, lactic acid, benzoic acid, salicylic acid, thymol, 2-benzyl-4-chlorophenol, 2,2'-methylene-bis-(6-bromo-4-chlorophenol), 2,4,4'-trichloro-2'-hydroxydiphenyl ether, N-(4-chlorophenyl)-N-(3,4-dichlorophenyl)urea, N,N'-(1,10-decanediyldi-1-pyridinyl-4-ylidene)-bis-(1-octanamine)dihydrochloride, N,N'-bis-(4-chlorophenyl)-3,12-diimino-2,4,11,13-tetraazatetradecanediimideamide, quaternary surface-active compounds, guanidines. Preferred surface-active quaternary compounds contain an ammonium, sulfonium, phosphonium, iodonium, or arsonium group. Disinfecting essential oils, which simultaneously provide scenting of the virucidal treatment solution, can furthermore also be used. Particularly preferred active substances are selected, however, from the group encompassing salicylic acid, quaternary surfactants, in particular benzalkonium chloride, peroxo compounds, in particular hydrogen peroxide, alkali metal hypochlorite, as well as mixtures thereof. A further disinfecting ingredient of this kind is contained in the surfactant preparation, for example, in a quantity from 0.01 to 1 wt %, by preference 0.02 to 0.8 wt %, in particular 0.05 to 0.5 wt %, particularly preferably 0.1 to 0.3 wt %, extremely preferably 0.2 wt %.

Liquid surfactant preparations according to the present invention in the form of solutions containing usual solvents are manufactured as a rule by simply mixing the ingredients, which can be placed into an automatic mixer as substance or as solution.

Surfactant preparations according to the present invention can contain only the hydrolytic enzyme as described. Alternatively, they can also contain further hydrolytic enzymes or other enzymes at a concentration useful for the effectiveness of the surfactant preparation. A further subject of the invention is thus represented by surfactant preparations that additionally encompass one or more further enzymes, all enzymes established in the existing art for these purposes being usable in principle. All enzymes that can display a catalytic activity in a surfactant preparation according to the present invention are preferably usable as further enzymes, in particular a protease, amylase, cellulase, hemicellulase, mannanase, tannase, xylanase, xanthanase, xyloglucanase, β-glucosidase, pectinase, carrageenase, perhydrolase, oxidase, oxidoreductase, or a lipase, as well as mixtures thereof. Further enzymes are contained in the surfactant preparation advantageously in a respective total quantity from $1\times10^{-8}$ to 5 weight percent, based on active protein. Each enzyme is contained in surfactant preparations according to the present invention preferably from 0.0001 to 1% and more preferably from 0.0005 to 0.5%, 0.001 to 0.1%, and particularly preferably from 0.001 to 0.06 wt %, based on active protein. Particularly preferably, the enzymes exhibit synergistic cleaning performance results with respect to specific stains or spots, i.e. the enzymes contained in the surfactant preparation mutually assist one another in terms of their cleaning performance. Very particularly preferably, a synergy of this kind exists between a contained protease and a further enzyme of an agent according to the present invention, thereamong in particular between the protease and a lipase and/or an amylase and/or a mannanase and/or a cellulase and/or a pectinase. Synergistic effects can occur not only between various enzymes, but also between one or more enzymes and further ingredients of the surfactant preparation according to the present invention.

In a surfactant preparation according to the present invention, the component stabilizing the hydrolytic enzyme can moreover encompass at least one further enzyme stabilizer. A further enzyme stabilizer of this kind is or encompasses, for example, a polyol, in particular glycerol, 1,2-ethylene glycol or propylene glycol, an antioxidant, glyceric acid, calcium ions or calcium compounds, lactate, or a lactate derivative. It can also involve one or more of those enzyme-stabilizing compounds which are disclosed in the international patent applications WO 07/113,241 A1 or WO 02/008398 A1. The interaction of oligoaminobiphenyl oligocarboxylic acid and the further enzyme stabilizer preferably results in synergistic enzyme stabilization. This is understood to be better enzyme stabilization by the combination of the two compounds as compared with enzyme stabilization by each one of said compounds alone, and also as compared with the sum of the individual performance results of the two compounds in terms of enzyme stabilization. A combination of corresponding compounds as the component stabilizing the hydrolytic enzyme thus makes it possible, for example, to use the stabilizers in surfactant preparations according to the present invention in lower concentrations in total. It is further possible to achieve improved enzyme stabilization with a component of this kind stabilizing the hydrolytic enzyme. In this regard, the further enzyme stabilizer does not necessarily need to be a boron-free stabilizer, since it is also possible, because of the interaction of the two compounds, to use a smaller quantity of a boron-containing compound in a surfactant preparation. For example, it is also possible in this regard to use a phenylboronic acid derivative having the structural formula

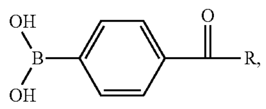

in which R denotes hydrogen, a hydroxyl group, a C1 to C6 alkyl group, a substituted C1 to C6 alkyl group, a C1 to C6 alkenyl group, or a substituted C1 to C6 alkenyl group, by preference 4-formylphenylboronic acid (4-FPBA), as a further enzyme stabilizer.

The further enzyme stabilizer is present in the surfactant preparation by preference in a concentration from 0.000001 to 10 wt %, and increasingly preferably from 0.00001 to 5 wt %, from 0.0001 to 2.5 wt %, from 0.001 to 2 wt %, from 0.01 to 1.5 wt %, and from 0.1 to 1 wt %.

A further subject of the invention is the use of a component that encompasses an oligoaminobiphenyl oligocarboxylic acid to stabilize a hydrolytic enzyme in a liquid surfactant preparation.

The reason is that, as set forth above, this component brings about an advantageous stabilization of the hydrolytic enzyme in a liquid surfactant preparation. The hydrolytic enzyme is by preference a protease.

All facts, subjects, and embodiments that are described for surfactant preparations according to the present invention are also applicable to this subject of the invention. Reference is therefore made at this junction expressly to the disclosure at the corresponding location, with the instruction that said disclosure also applies to the present use according to the present invention.

A further subject of the invention is a method in which a hydrolytic enzyme is stabilized in a washing bath by a component that stabilizes the hydrolytic enzyme and encompasses an oligoaminobiphenyl oligocarboxylic acid.

The reason is that, as set forth above, this component brings about an advantageous stabilization of the enzyme in a liquid surfactant preparation. The hydrolytic enzyme is consequently also stabilized in the corresponding washing or cleaning bath whose basis is the liquid surfactant preparation. The method is preferably a washing, cleaning, or disinfecting method. Particularly preferably, a surfactant preparation as described above is utilized in such a method. By preference, the hydrolytic enzyme is selected from the group consisting of protease, amylase, cellulase, glycosidase, hemicellulase, mannanase, xylanase, xyloglucanase, xanthanase, pectinase, β-glucosidase, carrageenase, lipase, or mixtures thereof. Particularly preferably, the hydrolytic enzyme is a protease.

A method according to the present invention preferably occurs in a temperature range between 10° C. and 60° C., in particular between 10° C. and 50° C., between 10° C. and 40° C., between 10° C. and 30° C., and particularly preferably between 15° C. and 30° C. Thermally stable hydrolytic enzymes could also be used in methods according to the present invention even at temperatures higher than 60° C., for example up to 70° C. or 75° C. The pH at which a method according to the present invention is advantageously carried out can be dependent on the object to be treated. For example, a surfactant preparation that is based on a cleaning agent for toilets advantageously has an acid pH, for example a pH between pH 2 and pH 5. A surfactant preparation that is based on a textile washing agent or a cleaning agent for other hard surfaces advantageously has a slightly acid, neutral, or alkaline pH, for example a pH between pH 6 and pH 11 or between pH 7 and pH 10. A surfactant preparation that is based on a hand dishwashing agent has, for example, a pH of between pH 6.5 and pH 8. It is consequently advantageous also to carry out a method according to the present invention at these respective pH values.

All facts, subjects, and embodiments that are described for surfactant preparations according to the present invention are also applicable to this subject of the invention. Reference is therefore made at this junction expressly to the disclosure at the corresponding location, with the instruction that said disclosure also applies to methods according to the present invention.

A further subject of the invention is a liquid enzyme preparation encompassing a hydrolytic enzyme and a component stabilizing the hydrolytic enzyme, which is characterized in that the component stabilizing the hydrolytic enzyme encompasses an oligoaminobiphenyl oligocarboxylic acid, in particular a diaminobiphenyl dicarboxylic acid, and particularly preferably 3,3-diamino-[1,1-biphenyl]-2,4-dicarboxylic acid. It has been determined that a component stabilizing the hydrolytic enzyme as described above also stabilizes a hydrolytic enzyme in a liquid preparation that encompasses no surfactant. With such a component it is consequently possible also to stabilize hydrolytic enzymes in a culture supernatant of a fermentation, during the processing of a culture supernatant of a fermentation, or in a liquid enzyme preparation. By preference, the oligoaminobiphenyl oligocarboxylic acid is contained in the preparation in a quantity from 0.000001 to 10 wt %, and/or the hydrolytic enzyme is contained in a quantity from $1\times10^{-8}$ to 5 wt %, based on active protein. Also preferably, the hydrolytic enzyme is a protease. All further facts, subjects, and embodiments that are not applicable exclusively to surfactant preparations according to the present invention are consequently also applicable to this subject of the invention. Reference is therefore made at this junction expressly to the disclosure at the corresponding location, with the instruction that said disclosure also applies to liquid enzyme preparations according to the present invention.

EXAMPLE

Stabilizing a Protease in a Liquid Washing Agent According to the Present Invention A liquid washing agent of the following composition served as a baseline washing agent formulation (all indications in percent by weight): 0.3 to 0.5% xanthan, 0.2 to 0.4% antifoaming agent, 6 to 7% glycerol, 0.3 to 0.5% ethanol, 4 to 7% FAEOS (fatty alcohol ether sulfate), 24 to 28% nonionic surfactants, 1 to 2% sodium citrate (dihydrate), 2 to 4% soda, 14 to 16% coconut fatty acids, 0.5% HEDP (1-hydroxy-ethane-(1,1-diphosphonic acid)), 0 to 0.4% PVP (polyvinylpyrrolidone), 0 to 0.05% optical brightener, 0 to 0.001% dye, remainder demineralized water.

The oligoaminobiphenyl oligocarboxylic acid 3,3-diamino-[1,1-biphenyl]-2,4-dicarboxylic acid was incorporated into this formulation as the component stabilizing the hydrolytic enzyme, as indicated below (see Table 1, indications in this regard in wt %). Comparison formulations that contained either boric acid as an enzyme stabilizer, or no enzyme stabilizer, served as controls. The protease used was variant F49 of the protease from *Bacillus lentus* in accordance with WO 95/23221 (quantity used: 1 wt % active substance).

in order to partly or entirely eliminate boric acid or boron-containing compounds as an enzyme stabilizer in a liquid surfactant preparation.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

```
                          SEQUENCE LISTING


<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Peptide part of suc-L-Ala-L-Ala-L-Pro-L-Phe-p-
      nitroanilide substrate for measurement of proteolytic activity

<400> SEQUENCE: 1

Ala Ala Pro Phe
1
```

Storage occurred in airtight sealed vessels at 30° C. over time periods of various lengths as indicated in Table 1. After storage, the respective residual proteolytic activity was determined by way of the release of the para-nitroaniline (pNA) chromophore from the suc-L-Ala-L-Ala-L-Pro-L-Phe-p-nitroanilide substrate (suc-AAPF-pNA) (SEQ ID NO. 1). The protease cleaves the substrate and releases pNA. The release of pNA causes an increase in extinction at 410 nm, the time course of which is an indication of enzymatic activity (see Del Mar et al., 1979). Measurement occurred at a temperature of 25° C., at pH 8.6 and at a wavelength of 410 nm. The measurement time was 5 min, with a measurement interval from 20 s to 60 s. The proteolytic activity values obtained are indicated in Table 1 below, based on an initial activity of 100% when storage began.

TABLE 1

Determining residual proteolytic activity after storage

| Washing agent per baseline formulation, plus | Initial | 13 days |
|---|---|---|
| 0.1% 3,3-diamino-[1,1-biphenyl]-2,4-dicarboxylic acid | 100% | 30.2% |
| 0.5% 3,3-diamino-[1,1-biphenyl]-2,4-dicarboxylic acid | 100% | 43.5% |
| 1.0% 3,3-diamino-[1,1-biphenyl]-2,4-dicarboxylic acid | 100% | 48.0% |
| 2.0% 3,3-diamino-[1,1-biphenyl]-2,4-dicarboxylic acid | 100% | 73.6% |
| 1% boric acid | 100% | 74.9% |
| no enzyme-stabilizing component | 100% | 25.2% |

It is evident that a component according to the present invention that stabilizes the hydrolytic enzyme produces an improvement in enzyme stability as compared with the control having no enzyme stabilizer. It can consequently be used

What is claimed is:

1. A liquid surfactant preparation comprising a hydrolytic enzyme and a component stabilizing the surfactant, a hydrolytic enzyme, wherein the component stabilizing the hydrolytic enzyme comprises an oligoaminobiphenyl oligocarboxylic acid selected from the group consisting of a) compounds having the formula (I)

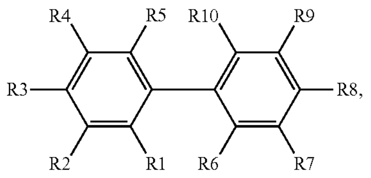

(I)

wherein R1, R2, R3, R4, R5, R6, R7, R8, R9, and R10 are each —$NH_2$, —COOH, or —H, wherein at least two of the residues R1 to R10 are —$NH_2$, and at least two of the residues R1 to R10 are —COOH and the further residues are —H, and b) derivatives of a) that are glycosylated, oxidized, N-methylated, N-formylated, or N-acylated on one or more amino groups.

2. The surfactant preparation according to claim 1, wherein the oligoaminobiphenyl oligocarboxylic acid is a diaminobiphenyl dicarboxylic acid.

3. The surfactant preparation according to claim 1, wherein the oligoaminobiphenyl oligocarboxylic acid is 3,3-diamino-[1,1-biphenyl]-2,4-dicarboxylic acid.

4. The surfactant preparation according to claim 1, wherein the oligoaminobiphenyl oligocarboxylic acid is contained in a quantity from 0.000001 to 10 wt %; and the hydrolytic enzyme is included in a quantity from $1\times10^{-8}$ to 5 weight percent, based on active protein.

5. The surfactant preparation according to claim 1, wherein the hydrolytic enzyme is selected from the group consisting of a protease, amylase, cellulase, glycosidase, hemicellulase, mannanase, xylanase, xyloglucanase, xanthanase, pectinase, β-glucosidase, carrageenrase, and a lipase, or is a mixture that encompasses at least two of said enzymes.

6. The surfactant preparation according to claim 1, wherein the preparation is a washing agent, cleaning agent, or disinfection agent.

7. The surfactant preparation according to claim 1, wherein the surfactant preparation moreover comprises at least one further ingredient that is selected from the group consisting of builder, nonaqueous solvent, acid, water-soluble salt, thickening agent, disinfecting ingredient, and combinations thereof.

8. A washing or cleaning method, comprising:

washing or cleaning with the liquid surfactant preparation of claim 1, wherein the hydrolytic enzyme is selected from the group consisting of protease, amylase, cellulase, glycosidase, hemicellulase, mannanase, xylanase, xyloglucanase, xanthanase, pectinase, β-glucosidase, carrageenase, lipase, and mixtures thereof.

9. A liquid enzyme preparation comprising a hydrolytic enzyme and a component stabilizing the hydrolytic enzyme, wherein the component stabilizing the hydrolytic enzyme comprises an oligoaminobiphenyl oligocarboxylic acid selected from the group consisting of a) compounds having the formula (I)

(I)

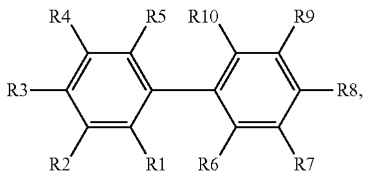

wherein R1, R2, R3, R4, R5, R6, R7, R8, R9, and R10 are each —$NH_2$, —COOH, or —H, wherein at least two of the residues R1 to R10 are —$NH_2$, and at least two of the residues R1 to R10 are —COOH and the further residues are —H, and b) derivatives of a) that are glycosylated, oxidized, N-methylated, N-formylated, or N-acylated on one or more amino groups.

10. The liquid enzyme preparation according to claim 9, wherein the oligoaminobiphenyl oligocarboxylic acid is a diaminobiphenyl dicarboxylic acid.

11. The liquid enzyme preparation according to claim 10, wherein the diaminobiphenyl dicarboxylic acid is 3,3-diamino-[1,1-biphenyl]-2,4-dicarboxylic acid.

* * * * *